(12) United States Patent
Gabriele et al.

(10) Patent No.: US 11,576,797 B2
(45) Date of Patent: *Feb. 14, 2023

(54) BORED HOLLOW LUMEN

(71) Applicant: THE SECANT GROUP, LLC, Telford, PA (US)

(72) Inventors: Peter D. Gabriele, Frisco, TX (US); Steven Lu, Cambridge, MA (US)

(73) Assignee: THE SECANT GROUP, LLC, Telford, PA (US)

( * ) Notice: Subject to any disclaimer, the term of this patent is extended or adjusted under 35 U.S.C. 154(b) by 334 days.

This patent is subject to a terminal disclaimer.

(21) Appl. No.: 16/755,209

(22) PCT Filed: Oct. 12, 2018

(86) PCT No.: PCT/US2018/055633
§ 371 (c)(1),
(2) Date: Apr. 10, 2020

(87) PCT Pub. No.: WO2019/075343
PCT Pub. Date: Apr. 18, 2019

(65) Prior Publication Data
US 2020/0253752 A1 Aug. 13, 2020

Related U.S. Application Data

(60) Provisional application No. 62/572,195, filed on Oct. 13, 2017.

(51) Int. Cl.
*A61F 2/82* (2013.01)
*A61L 31/06* (2006.01)
(Continued)

(52) U.S. Cl.
CPC ............. *A61F 2/82* (2013.01); *A61L 31/06* (2013.01); *A61L 31/148* (2013.01); *A61L 31/16* (2013.01);
(Continued)

(58) Field of Classification Search
None
See application file for complete search history.

(56) References Cited

U.S. PATENT DOCUMENTS

| 5,071,294 A | 12/1991 | Suzuki et al. |
| 5,383,925 A | 1/1995 | Schmitt |

(Continued)

FOREIGN PATENT DOCUMENTS

| JP | 4934269 B2 * | 5/2012 | ........... A61F 2/0077 |
| WO | 2014074134 A1 | 5/2014 | |

OTHER PUBLICATIONS

Wang et al. (A tough biodegradable elastomer, Nature Biotechnology, 20, 602-606, Jun. 1, 2002). (Year: 2002).*

*Primary Examiner* — Melissa S Mercier
(74) *Attorney, Agent, or Firm* — McNees Wallace & Nurick LLC

(57) ABSTRACT

A manufacturing process forms a bored hollow lumen. The manufacturing process includes providing a solid rod of a bioresorbable material and boring a hole axially through the solid rod. The manufacturing process also includes modifying surface defects formed on a luminal surface by the boring, the luminal surface defining the hole, thereby forming the bored hollow lumen. A bored hollow lumen includes a lumen wall including a bioresorbable material. The lumen wall has an abluminal surface and a luminal surface. The luminal surface defines a bore through the bored hollow lumen. The bioresorbable material has a uniform crosslinking density.

8 Claims, 2 Drawing Sheets

(51) Int. Cl.
*A61L 31/14* (2006.01)
*A61L 31/16* (2006.01)

(52) U.S. Cl.
CPC ... *A61F 2240/001* (2013.01); *A61L 2300/412* (2013.01)

(56) References Cited

U.S. PATENT DOCUMENTS

| | | | |
|---|---|---|---|
| 5,980,564 A * | 11/1999 | Stinson | A61L 27/18 606/191 |
| 8,192,348 B2 | 6/2012 | Tranquillo et al. | |
| 11,065,099 B2 * | 7/2021 | Lu | A61L 27/48 |
| 2001/0025131 A1 | 9/2001 | Edwin et al. | |
| 2004/0267351 A1 | 12/2004 | Swain | |
| 2006/0198750 A1 * | 9/2006 | Furst | C22C 27/04 419/42 |
| 2007/0055367 A1 | 3/2007 | Kutryk et al. | |
| 2007/0196423 A1 * | 8/2007 | Ruane | A61L 31/148 427/2.25 |
| 2009/0088836 A1 | 4/2009 | Bishop et al. | |
| 2014/0309726 A1 | 10/2014 | Wang | |
| 2015/0297380 A1 | 10/2015 | Serna et al. | |
| 2015/0320542 A1 | 11/2015 | Gabriele et al. | |
| 2016/0279303 A1 | 9/2016 | Zhang et al. | |
| 2017/0246316 A1 | 8/2017 | Wroblesky et al. | |

* cited by examiner

BORED HOLLOW LUMEN

CROSS-REFERENCE TO RELATED APPLICATIONS

This application claims priority to and the benefit of U.S. Provisional Application No. 62/572,195 filed Oct. 13, 2017, which is hereby incorporated by reference in its entirety.

FIELD OF THE INVENTION

The present invention relates to the field of implantable lumens, such as, for example, grafts to replace blood vessels. More specifically, the present invention relates to bored hollow lumens and methods of forming such lumens.

BACKGROUND

Cardiovascular disease is the leading cause of death worldwide. Although drug treatment of cardiovascular disease is increasing, two of the primary methodologies currently used to treat cardiovascular disease are coronary artery bypass grafts and percutaneous coronary intervention, commonly referred to as angioplasty.

During an angioplasty procedure, a stent is often implanted into a restricted blood vessel to open the diameter of the blood vessel. Various types of stents are currently known for such procedures. Each type of stent has certain advantages, but each type also suffers from one or more known complications or weaknesses, which may include, but are not limited to, restenosis, the need for long term use of anticoagulants, inhibition of natural blood vessel motion (such as pulsatile motion), in-stent thrombosis, improper healing, and potential for fracture of the stent.

In contrast to percutaneous coronary intervention, a coronary artery bypass graft is implanted to bypass a blockage or obstruction in a coronary artery. Various types of grafts have been used for bypass surgeries, including biological grafts (e.g. autografts, allografts and xenografts) and artificial grafts (e.g., polytetrafluoroethylene (PTFE), expanded PTFE (ePTFE), and poly(ethylene terephthalate) (PET)). Additionally, although not widely used, tissue-engineered grafts are being developed in which the graft is produced in vitro.

Although each of the known grafts has certain advantages, such as low cost, high availability, or high similarity to native tissue, each of the known grafts also suffers from one or more known complications or weakness. For instance, while autografts are the current gold standard because of their high durability, the lack of availability and donor site morbidity continue to be issues. Allografts typically take longer to integrate into the body and require extensive processing before they are suitable for implantation. Artificial grafts are readily available but may be more prone to infection, thrombosis, or intimal hyperplasia and may require long term use of medication, such as anticoagulants. Although tissue-engineered grafts overcome many of the problems associated with commonly-used biological and artificial grafts, tissue-engineered grafts are extremely expensive and take a long time to manufacture.

In general, native vessels remain the preferred choice for revascularization procedures, however, such tissues are not always available. In such cases, synthetic materials, such as ePTFE and PET, have been used successfully as vascular conduits when the graft diameter exceeds 6 mm. Results have been poor, however, with grafts less than 6 mm in diameter, due to the development of thrombi and intimal hyperplasia.

The use of textile technology to make three-dimensional hollow lumen structures is a well-known art. While flexible, water-impermeable lumens are described in U.S. Pat. App. Pub. No. 2015/0320542 (incorporated herein by reference) and work well, continued improvements are still desirable to further enhance the performance of such devices.

BRIEF DESCRIPTION OF THE INVENTION

The present disclosure relates to hollow lumens and a method of manufacturing hollow lumens from solid rods that produce precision wall thickness in the resulting lumens, including embodiments containing embedded braids as well as overbraided constructs.

Wall thickness in a synthetic vascular conduit, prosthetic nerve guide, or other hollow lumen organ tissue engineered construct of a bioresorbable material can have an impact in efficient in vivo degradation as well as in engineering properties in creating biomimetic features and benefits to the mechano-biologic simulation of a scaffold construct involved in endogenous regeneration.

Additionally, surface mechanics such as texture, topography, and finish are material to in vivo end use of such lumens. For instance, rough interior surfaces of a vascular conduit can modify hemodynamic flow at the abluminal wall, causing disruption in local flow dynamics, as well as trauma to the fragile endogenous cells involved in the act of homesteading onto such surfaces. While porosity is not necessary for efficient homesteading of endoluminal tissue, a rough surface resulting from deficiencies in manufacturing can be fatal to the efficiency of tissue attachment.

In some embodiments, a manufacturing process forms a bored hollow lumen. The manufacturing process includes providing a solid rod of a bioresorbable material and boring a hole axially through the solid rod. The manufacturing process also includes modifying surface defects formed on a luminal surface by the boring, the luminal surface defining the hole, thereby forming the bored hollow lumen.

In some embodiments, a bored hollow lumen includes a lumen wall including a bioresorbable material. The lumen wall has an abluminal surface and a luminal surface. The luminal surface defines a bore through the bored hollow lumen. The bioresorbable material has a uniform crosslinking density.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Exemplary embodiments create a precision wall thickness in a manufactured lumen, while at the same time providing a way to finish the luminal and abluminal surfaces. In this manner, exemplary embodiments contemporaneously create a finished lumen having both precision inner diameter dimensions and construct thickness.

Among the advantages of exemplary embodiments are that the manufacturing methods described herein can substantially reduce production cost and improve process control and quality requirements in precision manufacturing important in medical device applications.

Figure 1:
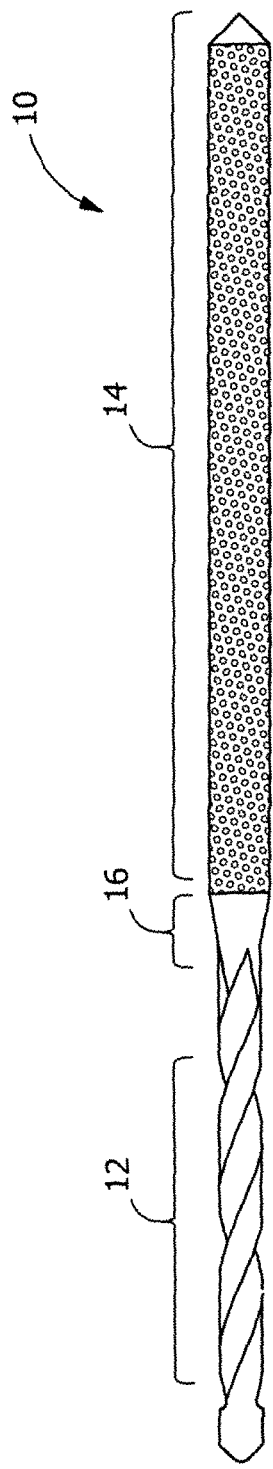
FIG. 1 shows a boring tool providing a combination of boring and burnishing in an exemplary embodiment.

FIG. 1 shows a boring tool 10 having a cutting portion 12 including a cutting bit, a burnishing portion 14 including a burnishing surface, and a transition portion 16 between the cutting portion 12 and the burnishing portion 14. The transition portion 16 transitions between the smaller diameter of the cutting portion 12 and the larger diameter of the burnishing portion 14. Alternatively, separate tools may be used to provide the boring and burnishing features.

Figure 2:
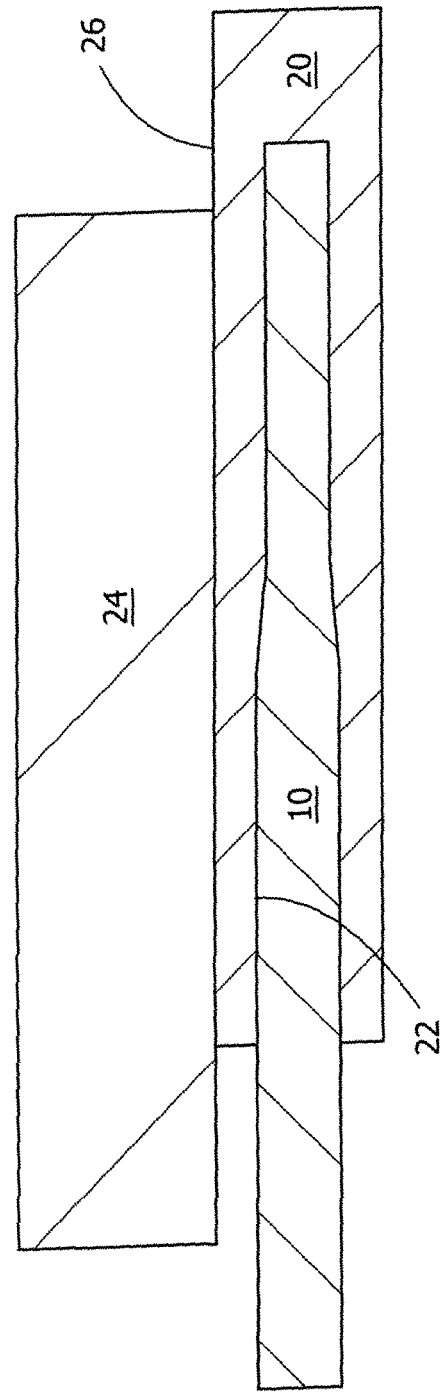
FIG. 2 schematically shows a process of manufacturing a bored hollow lumen in an exemplary embodiment.

FIG. 2 schematically shows a solid rod 20 in the process of being bored and burnished by a boring tool 10. The solid rod 20 is cylindrical in shape with a circular cross section. The surface burnished by the solid boring tool 10 becomes the luminal surface 22 of the resulting bored hollow lumen. A calender roll 24 is shown applying a texture to the surface that becomes the abluminal surface 26 of the resulting bored hollow lumen. In some embodiments, the burnishing removes surface defects formed by the boring and smooths the luminal surface 22.

The solid rod 20 may be composed entirely of a bioresorbable polymer resin or may include one or more additional components. In some embodiments, the solid rod 20 contains one or more drugs, medicaments, or other biologically- and/or pharmaceutically-active ingredients, which may be incorporated therein for controlled release during subsequent resorption or degradation of the bioresorbable material due to the surface-eroding characteristics, such as when the bioresorbable material is PGS.

Figure 3:
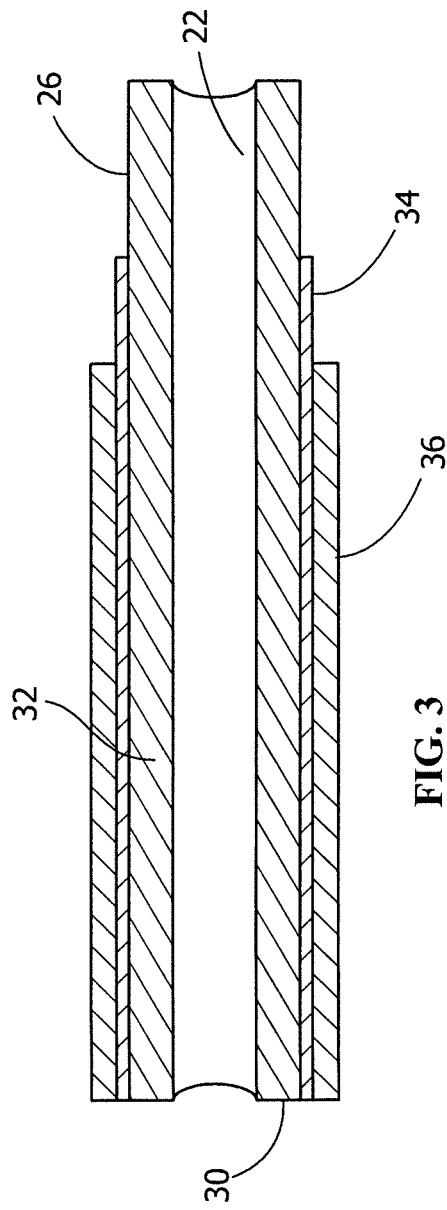
FIG. 3 shows a schematic cross sectional view of an overbraided solid rod in an exemplary embodiment.

FIG. 3 schematically shows a bored hollow lumen 30 including a lumen wall 32, a luminal surface 22, and an abluminal surface 26. An overbraid 34 is formed over the abluminal surface 26 and an outer coating 36 covers the overbraid 34. The outer coating 36 may be applied by co-extrusion with the solid rod 20 or may be otherwise applied to the overbraid 34. The outer coating 36 may be applied as a coating composition or a sealing composition that seals the overbraid 34. In other embodiments, the outer coating 34 may be applied directly to the abluminal surface 26 without an overbraid 34 being applied.

In one embodiment, the bored hollow lumen 30 is formed of a bioresorbable material, such as, for example, poly (glycerol sebacate) (PGS), including all fowls of PGS, such as neat PGS as well as PGS co-polymers, including PGS-urethane copolymers sometimes referred to as PGSU. Any other bioresorbable material suitable for use in hollow lumen organ tissue engineering applications may also be used. In some embodiments, the bioresorbable material is capable of being crosslinked to form a thermoset elastomer.

The employed bioresorbable material is processed into solid rod 20 stock. Forming bored hollow lumens 30 from solid rod 20 stock has the advantage of starting with a material having a uniform crosslink density, which aids in uniform degradation kinetics.

The solid rod 20 stock is then subjected to a boring operation preferably using a boring tool 10, as shown in FIG. 1, in which a cutting portion 12 of the boring tool 10 having a precise cutting diameter and fixed length translates into a burnishing portion 14 having burnishing surface that extends proximally from the distal cutting bit. The boring tool 10 may be designed for various bore hole diameters but in some embodiments is sized to create a final bore size of less than 6 mm, such as about 3 mm or less or such as about 2 mm to about 3 mm. Exemplary embodiments are particularly useful for construction of small-bore lumens to replace vessels having an inner diameter of 6 mm or less, such as those as small as 3 mm. The boring tool 10 may include a transition portion 16 between the cutting bit and the burnishing surface that expands slightly in diameter to match the final bore inner diameter.

In some embodiments, the wall thickness-to-inner diameter ratio is greater than 0.02, alternatively in the range of 0.03 to 0.07, alternatively in the range of 0.05 to 0.07, or any value, range, or sub-range therebetween. For a bored hollow lumen having a 2.5-mm inner diameter, the wall thickness of the bored hollow lumen may range from 200 µm to 1200 µm in thickness, preferably from 200 µm to 500 µm.

In an exemplary process, the solid rod 20 of the bioresorbable material is fixed within a jig or other holder to maintain longitudinal concentricity between the theoretical central axis of the solid rod 20 and parallel to the peripheral surface of the solid rod. This is intended to stabilize the bulk of the solid rod 20 during the boring process.

The boring tool 10 is then presented to the theoretical center point of the long axis of the solid rod 20 such that the cutting produces a precision bore and the concomitant luminal surface 22 to abluminal surface 26 are uniform. Once the cutting has commenced and has then completed the roughed-out bore, the burnishing surface continues to travel through the lumen, polishing the luminal surface 22 to remove defects.

The burnishing surface of the boring tool 10 preferably reduces or eliminates any surface features that might disrupt luminal fluid dynamics in vivo. Additionally, the burnishing surface of the boring tool 10 may be heated, lubricated, treated with an embedding agent, embossed, scored, or surfaced with any additional design to transfer a feature to the luminal surface 22, if desired.

In some embodiments, an exterior calendering roll 24 may be applied to the exterior abluminal surface 26 of the formed lumen to provide stability, compression, or surface featuring.

An exemplary manufacturing process overcomes variations in wall thickness and associated defects that may occur in other manufacturing processes. This manufacturing process also allows for the fabrication of both embedded braid and overbraid lumen constructs, although it will be appreciated that the manufacturing process is not limited to braided structures and may include other examples of textile luminal constructs, such as, for example, warp-knit and crocheted embodiments. Alternatively, the bored hollow lumen 30 may be formed free of any overlying or embedded textile structure.

Exemplary embodiments allow the manufacturing process to be fully automated to achieve a precision end-product and allows the engineer the option to precisely create a uniform degree of crosslink and wall thickness in a bored hollow lumen 30. Further, bore diameter is not dictated by braid diameter, providing the option to create smaller bore structures, but may also be used in larger bore vascular structures, where a non-linear anatomy is required.

The solid rod 20 stock that is subject to the manufacture processing may be overbraided with fibers of a bioresorbable material, including, but not limited to, polyglycolide (PGA), polylactide (PLA), poly(lactic-co-glycolic acid) (PLGA), or PGS. The addition of the overbraid 34 may aid in providing increased burst strength, kink resistance, and stability to the resulting bored hollow lumen 30. In some embodiments, the overbraid 34 is fixed to the solid rod 20 by a simple dip coating of PGS. In some embodiments, the bioresorbable resin of the dip coating infiltrates some of the space within the overbraid 34, such that upon curing of the dip coated resin, the overbraid 34 is laminated to the underlying solid rod 20. In some embodiments, the overbraid 34 is heat embedded into the rod by calender rolling.

Alternatively, the solid rod 20 may be left neat and free of any overbraid 34 or embedded braiding.

It will be appreciated that the boring process may be the last step, such as, for example, when heat-sensitive materials are used that would be negatively impacted by exposure to heat. In another embodiment, a solid rod 20 with an overbraid 34 may thereafter be co-extruded to provide a thicker outer covering 36 and embedding of the original overbraid 34, resulting in the original overbraid 34 being embedded within the portion of the solid rod 30 that becomes the lumen wall 32, as shown in FIG. 3.

The overbraid 34 may be pre-wetted or treated to increase penetration of the co-extruded PGS or other bioresorbable material forming the outer coating 36.

Exemplary embodiments allow for the control of the degree of polymerization of the bioresorbable material in the final construct prior to any braiding and thus with less concern for conditions of the curing step that might otherwise destroy the morphological properties of the braid yarn polymer.

It will be appreciated that the bored hollow lumen 30 may alternatively be manufactured from the solid rod 20 using laser ablation to bore the hole instead of a mechanical boring tool 10.

Exemplary embodiments also permit the formation of bored hollow lumens 30 from low molecular weight PGS, such as, for example, PGS having a weight average molecular weight less than 10,000 Da, alternatively between 5,000 Da and 10,000 Da, which may be frozen and then drilled.

Embodiments that employ a boring tool 10 having a burnishing portion 14 may include a hollow and perforated burnishing tool that simultaneously delivers an inner coating onto or into the lumen wall 32 at the luminal surface 22 during the burnishing process. In some embodiments, the inner coating is a passivation coating of resin and/or an infusion of biological agents.

In some embodiments, the interior of the lumen wall 32 may be reinforced by a bioresorbable stent, if desirable.

In embodiments where the porosity or the lumen wall 32 is important, micropores may be formed in the rod, such as, for example, by laser ablation, prior to, during, or after the boring operation.

In embodiments including an overbraid 34, the manufacturing process may include creating a solid rod 20 of PGS or other bioresorbable material having a predetermined cross-link level. The solid rod 20 may be fully cured or, in some embodiments, partially cured to a point for further processing to form a desired feature followed by a final cure. The overbraid 34 is then formed over the outer wall of the solid rod 20. The overbraid 34 may be heat-set or dip coated for stability. The solid rod 20 with the overbraid 34 is then fixed in a jig and bored out and burnished with the boring tool 10.

In embodiments employing an embedded overbraid 34, the manufacturing process may proceed generally the same as just described except that prior to boring, the overbraid 34 is embedded, such as, for example, by co-extruding or otherwise applying an outer coating 36 overtop the overbraid 34 such that the overbraid 34 (or other textile overlaying the solid rod 20 stock) is embedded within the final solid rod 20 structure prior to boring. The solid rod 20 is then heat fixed, cured, and bored.

In some embodiments, the luminal surface 22 of the bored hollow lumen 30 is patterned with an embossing tool. For example, the burnishing portion 14 may be further extended to include a fixed embossed pattern that is pressed into the finished burnished luminal surface 22. For example, in a bored hollow lumen 30 for use as a nerve conduit, longitudinal ridges may be embossed to promote contour guidance.

In some embodiments, the solid rod 20 is created from a two-part urethane flowable resin and "hardened" or "cured" to have a final physical property where heat-sensitive biologics may be added that are not compromised by the isocyanate chemistry of the two-part urethane.

Figure 4:
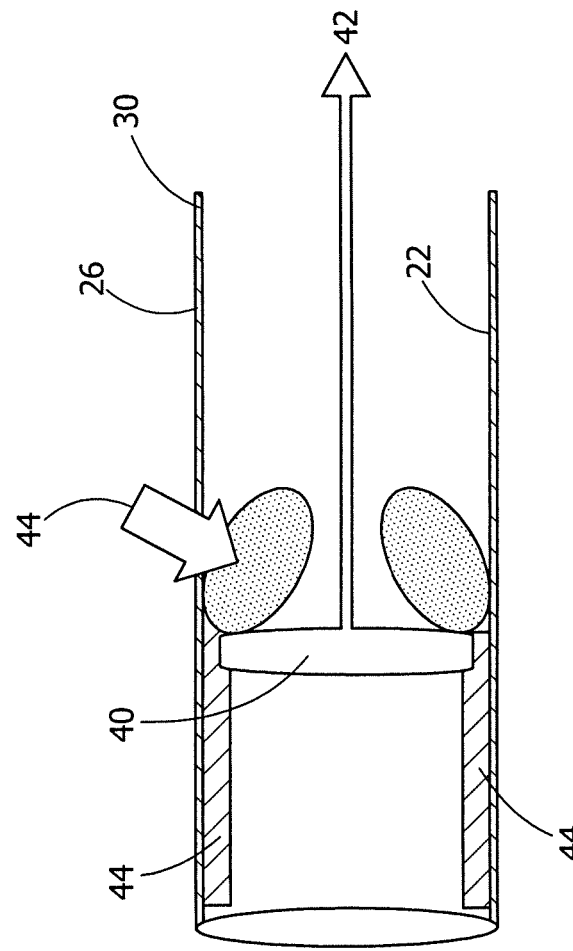
FIG. 4 schematically shows a process of coating a bored hollow lumen in an exemplary embodiment.

FIG. 4 shows the luminal surface 22 of the lumen wall 32 of a bored hollow lumen 30 being "pave coated", where a paver disc 40 of a slightly smaller diameter than the inner diameter of the luminal surface 22 coats the luminal surface 22 by drawing or plunging the paver disc 40 in an axial direction 42 to apply an inner coating 44 through the longitudinal structure.

In some embodiments, the outer coating 36 or the inner coating 44 includes one or more additives, which may include, but are not limited to, wound care agents, nutritional doping/bioactive agents, active pharmaceutical ingredients, biologic agents, drug agents, gene transfer technology agents, co-polymer particle development agents, and/or island agents in the sea matrix dissolution. In some embodiments, the additive encourages endothelial cell growth, such as, for example, a PGS-arginine adduct.

In some embodiments, the burnishing or a separate modification process micro-grooves, embosses, bores, scores, and/or micro-architects the luminal surface 22 or the abluminal surface 26. In some embodiments, the modification to the luminal surface 22 or the abluminal surface 26 promotes endothelial cell growth or encourages contour guidance of endothelial cells.

In some embodiments, straight line bores may be heat-fixed or post-cured to be crosslinked into a final non-linear configuration where, for instance, a curved aortic structure is desired or a cardiovascular and orthopedic shape is required.

In some embodiments, a solid rod 20 may be compressed and molded into a specific shape and fitted with a heat-shrinking textile to provide external support.

It should be understood that while the invention has been described with reference to one or more embodiments, various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention. In addition, all numerical values identified shall be interpreted as though the precise and approximate values are both expressly identified.

What is claimed is:

1. A bored hollow lumen comprising:
a lumen wall comprising a bioresorbable material, the lumen wall having an abluminal surface and a luminal surface, the luminal surface defining a bore through the bored hollow lumen; and
an overbraid on the abluminal surface;
wherein the bioresorbable material has a uniform cross-linking density.

2. The bored hollow lumen of claim 1, wherein the bioresorbable material is poly(glycerol sebacate).

3. The bored hollow lumen of claim 1 further comprising an outer coating over the overbraid.

4. The bored hollow lumen of claim 1 further comprising an inner coating on the luminal surface.

5. The bored hollow lumen of claim 1, wherein the inner coating comprises at least one additive encouraging endothelial cell growth on the luminal surface.

6. The bored hollow lumen of claim 1, wherein the lumen wall has a uniform radial thickness.

7. The bored hollow lumen of claim 1, wherein the luminal surface defines a bore hole having a diameter of less than 6 mm.

8. The bored hollow lumen of claim 1, wherein the luminal surface has a surface feature selected from the group consisting of microgrooves, an embossment, bores, scores, a microarchitecture, and combinations thereof.

* * * * *